US00PP29262P3

(12) United States Plant Patent
Olesen

(10) Patent No.: US PP29,262 P3
(45) Date of Patent: May 1, 2018

(54) MINIATURE ROSE PLANT NAMED 'POULPAR098'

(50) Latin Name: ***Rosa* hybrid**
Varietal Denomination: Poulpar098

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days. days.

(21) Appl. No.: 15/330,297

(22) Filed: Sep. 6, 2016

(65) Prior Publication Data

US 2018/0070505 P1 Mar. 8, 2018

(51) Int. Cl.
*A01H 5/02* (2006.01)

(52) U.S. Cl.
USPC ..... Plt./121

(58) Field of Classification Search
USPC ..... Plt./121
CPC ..... A01H 5/0222
See application file for complete search history.

(56) References Cited

PUBLICATIONS http://www.poulsenroser.com/assortment/rose-collections/parade/selina.aspx; No date; 1 page.*

* cited by examiner

*Primary Examiner* — Kent L Bell

(57) ABSTRACT

A new garden rose plant of the Miniature class which has abundant, pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulpar098'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpar098', originated as a single seedling from the stated cross.

The new variety may be distinguished from its male pollen parent and female seed parent primarily by the following characteristics. The male pollen parent plant has near white flowers, while the new variety has pink flowers. The female seed parent plant has orange red flowers, while the new variety has pink flowers.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar098' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpar098' was selected in the spring of 2011 by the inventor as a single plant from the progeny of the aforementioned hybridization.

Asexual reproduction of 'Poulpar098' by traditional budding and rooted cuttings was first done by Mogens N. Olesen in the nursery in Fredensborg, Denmark in July, 2011. This initial and other subsequent asexual propagations conducted in controlled environments have demonstrated that the characteristics of 'Poulpar098' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar098'.

Specifically illustrated in FIG. 1 are open flowers viewed from above and the side, and a flower bud upon opening.

DETAILED DESCRIPTION OF THE VARIETY

Figure 1:
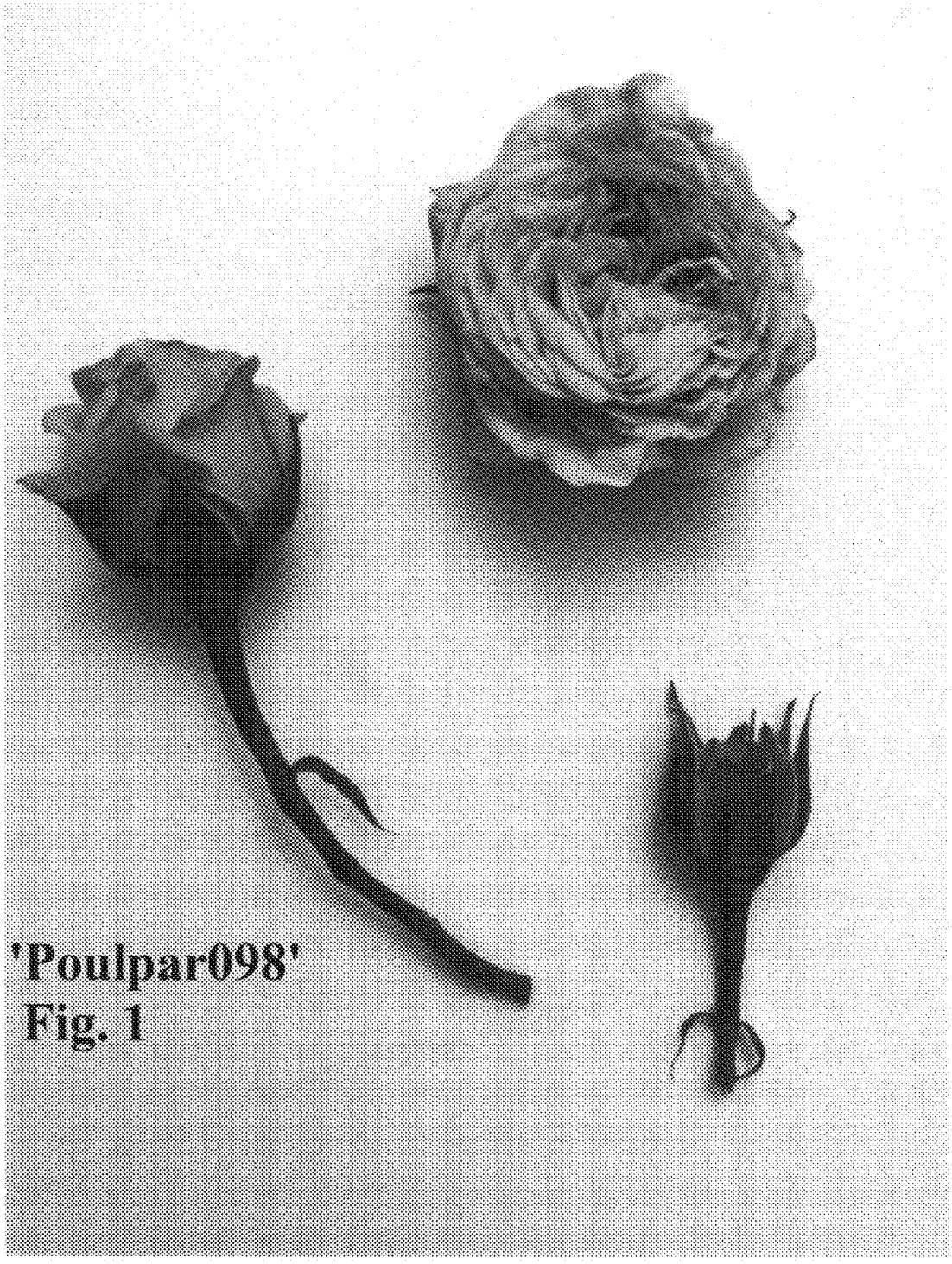
Figure 2:
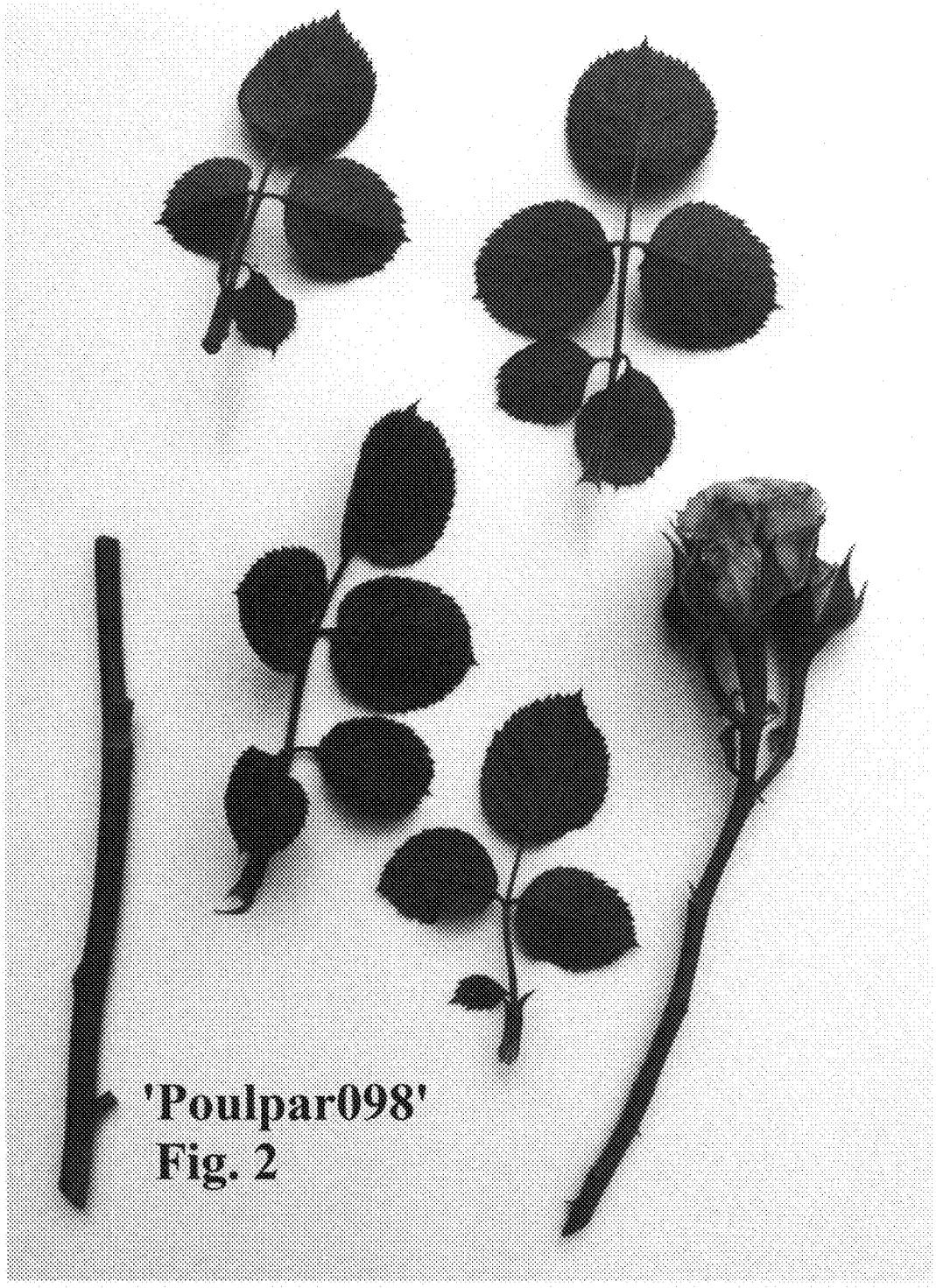
FIG. 2 shows bare stems, leaves, and a cluster of flowers opening on a branch. Plants shown are 2 years of age.

The following is a description of 'Poulpar098', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'POULhi008', U.S. Plant Pat. No. 15,722 are compared to 'Poulpar098' in Chart 1.

CHART 1

| | 'Poulpar098' | 'POULhi008' |
|---|---|---|
| Petal Count | 75 | 40 to 45 |
| Flower Diameter | 45 mm | 80 mm |
| General Tonality of Flower Color | Red Purple Group 62A. | Red Group 55B |

FLOWER AND FLOWER BUD

Blooming habit: Continuous.

Flower bud:

*Size*.—Upon opening, 15 mm in length from base of receptacle to end of bud. Bud diameter is 17 mm.

*Bud form*.—Ovoid.

*Sepal inner surface*.—Color: Yellow-Green Group 147C. Surface: Lightly pubescent.

*Sepal outer surface*.—Color: Yellow-Green Group 144A with intonations of Greyed-Red Group 180A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—20 mm long, 8 mm wide.

*Receptacle*.—Texture: Smooth. Size: 5 mm long, 7 mm wide. Color: Yellow-Green Group 144A. Shape: Campanulate.

*Pedicel*.—Surface: Smooth. Length: 20 mm. Diameter: 3 mm on average. Color: Yellow-Green Group 144A with intonations of Greyed-Orange Group 175A. Strength: Strong.

Flower bud development: Flower buds are borne in clusters of 3 to 5 flower buds per stem.

Flower bloom:

*Fragrance*.—None.

*Duration*.—The blooms have a duration on the plant of approximately 14 days. Petals fall cleanly away from plant after flowers have fully matured.

*Size*.—Flower diameter is 45 mm when open. Flower depth is 25 mm.

*Flower shape*.—High centered, double, with a high pointed center which is tightly closed.

*Shape of flower, side view*.—The upper portion is flat. The lower portion is concave.

Petalage: Under normal conditions, flowers have about 75 petals.

General tonality of flower: Open flowers are Red Purple Group 62A.

Petal color:

*Outer petals and inner petals*.—Upper surface: Red-Purple Group 62B. Lower surface: Red Group 55B.

*Basal petals spots*.—Upper surface: Yellow-Green Group 145D. Lower surface: Yellow-Green Group 145D.

Petals:

*Petal reflex*.—Partially reflexed.

*Margin*.—Entire and uniform with an occasional point at the center of the margin.

*Shape*.—Generally broad ellipse. Apex shape: Rounded. Base shape: Acute.

*Size*.—Up to 20 mm (l)×24 mm (w).

*Texture*.—Smooth.

*Thickness*.—Average.

Reproductive flower parts:

*Pollen*.—None observed.

*Anthers*.—Size: 1 mm in length. Color: Yellow Group 3C. Quantity: 28 on average.

*Filaments*.—Color: Yellow Group 11D. Length: 4 mm.

*Pistils*.—Length: 5 mm. Quantity: 20 on average.

*Stigmas*.—Color: Green-White Group 157A.

*Styles*.—Color: Green-White Group 157A.

*Location of stigmas*.—Level in location relative to the length of the filaments and the height of the anthers.

*Hips*.—None Observed.

PLANT

Plant growth: Upright, bushy. Plants are 30 cm in height, and 30 cm wide.

Stems:

*Color*.—Juvenile growth: Yellow-Green Group 144B. Mature growth: Yellow-Green Group 144A with intonations of Greyed-Orange Group 177A.

*Length*.—On average, canes are 15 cm from the base of the plant to the flowering portion.

*Diameter*.—5 mm.

*Internodes*.—On mature canes about 30 mm between nodes.

*Surface texture*.—Young wood: Smooth. Older wood: Smooth.

Long prickles:

*Incidence*.—About 8 prickles per 10 cm of stem.

*Size*.—Average length of prickles on mature stems is 6 mm.

*Shape*.—Upper portion is linear. Lower portion is concave.

*Color*.—Juvenile prickles: Greyed-Red Group 180A. Mature prickles: Greyed-Red Group 180A.

Plant foliage:

*Compound leaf*.—105 mm (l)×70 mm (w).

*Quantity*.—2 to 3 leaves per 10 cm of stem on average.

*Leaf bearing angle to the stem*.—45 degrees.

*Color of juvenile foliage*.—Upper side: Greyed-Purple Group N186C. Lower side: Greyed-Purple Group N186C.

*Color of mature foliage*.—Upper side: Yellow-Green Group 146A. Lower side: Yellow-Green Group 146B.

Plant leaves and leaflets:

*Stipules*.—Size: 15 mm long, 4 mm wide. Quantity: 2 per compound leaf. Shape: Linear, slightly broad based with outward extending apices. Margins: Finely serrated. Color: Yellow-Green Group 144A.

*Petiole*.—Length: About 20 mm. Diameter: 2 mm.

*Upper surface*.—Color: Yellow-Green Group 144A.

*Lower surface*.—Color: Yellow-Green Group 144A.

*Rachis*.—Length: About 40 mm. Diameter: About 1.5 mm. Upper surface: Color: Yellow-Green Group 144A.

*Lower surface*.—Color: Yellow-Green Group 144A. Observations: Small prickles.

*Leaflet*.—Quantity: Normally 5 leaflets. Margins: Serrated. Size: On average terminal leaflets are 35 mm long, 32 mm wide. Shape: Generally rounded. Base: Rounded. Apex: Round and slightly cuspidate. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpar098', substantially as illustrated and described herein, due to its abundant pink flowers, disease resistance, and extended period of bloom.

* * * * *

'Poulpar098'

'Poulpar098'